(12) United States Patent
Suto et al.

(10) Patent No.: US 12,208,112 B2
(45) Date of Patent: Jan. 28, 2025

(54) COMPOSITION FOR TREATING BLOOD CANCER USING 4'-THIO-5-AZA-2'-DEOXYCYTIDINE AND USES THEREOF

(71) Applicants: Southern Research Institute, Birmingham, AL (US); PinotBio, Inc., Gyeonggi-do (KR)

(72) Inventors: Mark J. Suto, Homewood, AL (US); Rebecca Boohaker, Birmingham, AL (US); Doo Young Jung, Daejeon (KR); Jin Soo Lee, Gyeonggi-do (KR); Hyunyong Cho, Gyeonggi-do (KR)

(73) Assignees: Southern Research Institute, Birmingham, AL (US); Pinotbio, Inc., Gyeonggi-Do (KR)

( * ) Notice: Subject to any disclaimer, the term of this patent is extended or adjusted under 35 U.S.C. 154(b) by 0 days.

(21) Appl. No.: 17/238,182

(22) Filed: Apr. 22, 2021

(65) Prior Publication Data
US 2021/0330689 A1 Oct. 28, 2021

Related U.S. Application Data
(60) Provisional application No. 63/014,346, filed on Apr. 23, 2020.

(51) Int. Cl.
| | | |
|---|---|---|
| A61K 31/706 | (2006.01) | |
| A61K 9/00 | (2006.01) | |
| A61K 31/635 | (2006.01) | |
| A61P 35/02 | (2006.01) | |

(52) U.S. Cl.
CPC .......... *A61K 31/706* (2013.01); *A61K 9/0053* (2013.01); *A61K 31/635* (2013.01); *A61P 35/02* (2018.01)

(58) Field of Classification Search
None
See application file for complete search history.

(56) References Cited

U.S. PATENT DOCUMENTS

| | | |
|---|---|---|
| 5,591,722 A | 1/1997 | Montgomery et al. |
| 6,020,322 A | 2/2000 | von Borstel et al. |
| 8,846,628 B2 | 9/2014 | Etter et al. |
| 10,815,264 B2 | 10/2020 | Dousson et al. |
| 2006/0014949 A1 | 1/2006 | Redkar et al. |
| 2011/0218170 A1 | 9/2011 | Thottassery et al. |
| 2016/0312261 A1 | 10/2016 | Plasmia |
| 2017/0233429 A1 | 8/2017 | Kuniyoshi et al. |
| 2018/0008608 A1 | 9/2018 | Paolo et al. |
| 2019/0240210 A1 | 8/2019 | Seki et al. |
| 2020/0262860 A1 | 8/2020 | Ye et al. |

FOREIGN PATENT DOCUMENTS

| | | |
|---|---|---|
| EP | 1541581 | 6/2005 |
| KR | 20110015629 | 2/2011 |
| WO | WO 00/04866 | 2/2000 |
| WO | WO 2008/068615 A1 | 6/2008 |
| WO | WO2011/109012 A1 | 9/2011 |
| WO | WO 2011/109383 A1 | 9/2011 |
| WO | WO 2016/155593 | 10/2016 |
| WO | WO 2016/189055 A1 | 12/2016 |
| WO | WO 2016/068341 | 8/2017 |
| WO | WO 2019/152459 A1 | 8/2019 |
| WO | WO 2019/204637 | 10/2019 |
| WO | WO 2020/068657 A1 | 4/2020 |

OTHER PUBLICATIONS

Tiwari, et al. (2003) "Synthesis and anti-cancer activity of some novel 5-azacytosine nucleosides" Nucleosides, Nucleotides & Nucleic Acids 22(12):2161-2170.

International Search Report and Written Opinion issued by the International Search Authority on Jun. 21, 2021 for International Application No. PCT/US21/28726 filed on Apr. 21, 2021 (Applicant—Southern Research Institute) (9 pages).

Wishka et al. (2021) "The development of B-selective glycosylation reactions with benzyl substituted 2-deoxy-1,4-dithio-D-erythro-pentafuranosides: enabling practical multi-gram synthesis of 4'-Thio-2'-deoxycytidine (T-dCyd) and 5-aza-4'-thio-2'- deoxycytidine (aza-T-dCyd) to support clinical development," Nucleosides, Nucleotides & Nucleic Acids 40(1), Oct. 16, 2020.

Musther et al. (2014) "Animal Versus Human Oral Drug Bioavailability: Do they Correlate," *European Journal of Pharmaceutical Sciences* 57: 280-291.

Pubchem CID 49866753, created on Feb. 17, 2011.

Secrist et al. (1991) "Synthesis and biological activity of 2'-deoxy-4'-thio pyrimidine nucleosides" *Journal of Med. Chem.* 34(8): 2361-6.

Thottassery, et al. (2014) "Novel DNA methyltransferase-1 (DNMT1) depleting anticancer nucleosides, 4'-thio-2'-deoxycytidine and 5-aza-4'-thio-2'-deoxycytidine" *Cancer Chemother Pharmacol* 74(2): 291-302.

Uenishi et al. (1994) "Syntheses and antitumor activities of D- and L-2'-deoxy-4'-thio pyrimidine nucleosides" *Nucleosides & Nucleotides* 13(6-7): 1347-61.

Fenaux et al. (2016) "A randomized, open-label, phase II study of CC-486 (oral azacitidine), alone or in combination with durvalumab (MEDI4736), in patients (pts) with myelodysplastic syndromes (MDS) unresponsive to prior parenteral azacitidine or decitabine," *Journal of Clinical Oncology* 34:15_suppl: TPS7078-TPS7078.

(Continued)

*Primary Examiner* — Patrick T Lewis
(74) *Attorney, Agent, or Firm* — Ballard Spahr LLP

(57) ABSTRACT

The present invention relates to pharmaceutical compositions for treating blood cancer, which includes 4'-thio-5-aza-2'-deoxycytidine (Aza-T-dCyd), and methods of treating blood cancer using a composition for oral administration that includes Aza-T-dCyd. The present invention provides a significant blood cancer therapeutic effect without having toxicity in a blood cancer mouse model or a human even with the Aza-T-dCyd dose conventionally known to have toxicity. This abstract is intended as a scanning tool for purposes of searching in the particular art and is not intended to be limiting of the present invention.

10 Claims, 9 Drawing Sheets

(56) References Cited

OTHER PUBLICATIONS

Forde et al., "Physical Nature of Interactions within the Active Site of Cytosine-5-methyltransferase", J. Phys. Chem. A, 2006, 110, 2308-2313.

Inoue et al., "Amplification of 4'-ThioDNA in the Presence of 4'-Thio-dTTP and 4'-Thio-dCTP, and 4'-ThioDNA-Directed Transcription in Vitro and in Mammalian Cells", 2007, 15424-15425.

Mei et al. (2015) "An open-label, single-arm, phase I/II study of lower-dose decitabine based therapy in patients with advanced hepatocellular carcinoma," *Oncotarget* 6(18): 16698-16711.

Ugo Pradere et al. (2014) "Synthesis of Nucleoside Phosphate and Phosphonate Prodrugs," *Chemical Reviews* 114(18): 9154-9218.

Youcef Mehellou et al. (2009) "Aryloxy Phosphoramidate Triesters: a Technology for Delivering Monophosphorylated Nucleosides and Sugars into Cells," *Chem Med Chem Communications* 4(11): 1779-1791.

Zeidner et al. (2016) "Phase I Clinical Trials in Acute Myeloid Leukemia: 23-Year Experience from Cancer Therapy Evaluation Program of the National Cancer Institute," *J. Natl. Cancer Inst.* 108(3): djv335.

Noriaki Hirayama, Handbook for preparation of organic compound crystals, Maruzen Publishing Co., Ltd., 2008, pp. 17-23, 37-40, 45-51, 57-65.

Loredana Cappellacci et al. (1999) Nucleosides and Nucleotides 18(4-5): 613-614.

COMPOSITION FOR TREATING BLOOD CANCER USING 4'-THIO-5-AZA-2'-DEOXYCYTIDINE AND USES THEREOF

CROSS-REFERENCE TO RELATED APPLICATIONS

This Application claims the benefit of U.S. Application No. 63/014,346, filed on Apr. 23, 2020, the contents of which are hereby incorporated by reference in their entirety.

BACKGROUND

DNA methyltransferase (DNMT) inhibitors based on cytidine analogues such as decitabine and azacytidine have excellent efficacy for treatment of elderly patients with myelodysplastic syndrome (MDS) and acute myelogenous leukemia (AML). However, there are many limitations. For example, many patients do not respond to decitabine or azacytidine. In addition, the therapeutic effect is limited due to side effects such as neutropenia, cytopenia, etc., even in the patients responding thereto. Finally, due to a poor PK profile, the therapeutic agent is generally used as an injection, so it suffers from low patient compliance.

4'-Thio-5-aza-2'-deoxycytidine (Aza-T-dCyd) is a novel DNMT1 inhibitor that was subjected to early clinical evaluation by the National Cancer Institute (NCI). This inhibitor has recently attracted attention due to high DNMT removal and inhibitory activities in cells, a reduced rate of degradation by cytidine deaminase, and a relatively low generation of toxic by-products compared to conventional compounds with a 5-azacytidine backbone. However, because Aza-T-dCyd shows high toxicity in blood cancer orthotopic models with blood cancers such as MDS and AML, the development of Aza-T-dCyd as an anticancer agent, which can be applied to a human patient, has been difficult. Specifically, it was reported in 2017 that even though Aza-T-dCyd was administered to ALL orthotopic xenograft models at a dose of 1.5 to 2.0 mg/kg, which is significantly lower than maximum tolerated doses (MTDs) for solid cancer models or other normal animals, severe toxicity was observed in the animals, indicating that further development was difficult. Moreover, it was also reported in 2018 that the toxicity of Aza-T-dCyd in MDS orthotopic animal models was so severe that therapeutic efficacy was not observed. In view of these studies, it was determined that the development of Aza-T-dCyd for the treatment of blood cancer is not likely to be successful.

Cytidine-based anticancer agents such as decitabine, azacytidine, etc., including Aza-T-dCyd, have problems in that, commonly, they are difficult to be developed as anticancer agents for oral administration due to a difference in rate or degree of uptake or metabolism per person in a human body. That is, although administered at the same amount, the cytidine-based anticancer agents have an extremely high variation in exposure based on an average drug exposure per person. In particular, the optimal dose for one individual may be a non-therapeutically effective for another, and can even be a dose that results in severe toxicity to still another, such that the therapeutic window becomes very narrow.

Korean Patent Application No. 10-2010-7028070 relates to an oral formulation of a cytidine analogue and a method of using the same, and provides a non-enteric composition for oral administration, which includes 5-azacytidine, not tetrahydrouridine. However, further studies of the anticancer effects of Aza-T-dCyd on blood cancer are still needed.

SUMMARY

In accordance with the purpose(s) of the invention, as embodied and broadly described herein, the invention, in one aspect, relates to pharmaceutical compositions for treating blood cancer, which include Aza-T-dCyd in a specific dosage range, and methods of treating blood cancer using a composition for oral administration including Aza-T-dCyd.

Thus, disclosed are pharmaceutical compositions comprising a therapeutically effective amount of a compound having a structure:

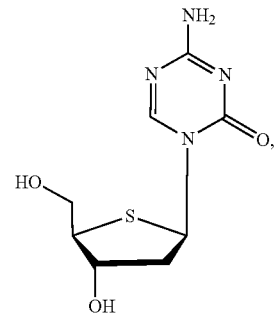

and a pharmaceutically acceptable carrier, wherein the therapeutically effective amount is of from about 5 mg/m² to no more than about 70 mg/m², and wherein the pharmaceutical composition is formulated for oral administration. In various further aspects, the therapeutically effective amount is of from about 30 mg/m² to no more than about 70 mg/m².

In various aspects, the therapeutically effective amount is of from about 5 mg/m² to no more than about 35 mg/m². In various further aspects, the therapeutically effective amount is of from about 5 mg/m² to no more than about 10 mg/m². In various further aspects, the therapeutically effective amount is of from about 30 mg/m² to no more than about 70 mg/m². In various further aspects, the therapeutically effective amount is of from about 35 mg/m² to no more than about 45 mg/m². In various further aspects, the therapeutically effective amount is of from about 45 mg/m² to no more than about 55 mg/m². In various further aspects, the therapeutically effective amount is of from about 55 mg/m² to no more than about 66 mg/m².

Also disclosed are pharmaceutical compositions for treating blood cancer, which includes Aza-T-dCyd of Formula 1 below and is orally administered at 5 to 70 mg/m²;

[Formula 1]

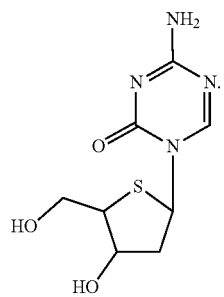

In various aspects, the pharmaceutical composition may be orally administered at 5 to 35 mg/m². In various further aspects, the pharmaceutical composition may be orally administered at 5 to 10 mg/m². In various further aspects, the pharmaceutical composition may be orally administered at 30 to 70 mg/m². In various further aspects, the pharmaceutical composition may be orally administered at 35 to 45 mg/m². In various further aspects, the pharmaceutical composition may be orally administered at 45 to 55 mg/m². In various further aspects, the pharmaceutical composition may be orally administered at 55 to 66 mg/m².

In various aspects, the administration may be performed in a cycle, which includes: (a) administration of the composition for 4 to 6 days; (b) a 1- to 3-day break after the administration (a); (c) administration of the composition for 4 to 6 days after the break (b); and (d) an 8- to 10-day break after the administration (c).

In various aspects, the blood cancer may be any one or more selected from the group consisting of non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma.

Also disclosed are methods of making a disclosed pharmaceutical composition.

Also disclosed are methods of treating a blood cancer in a human subject in need thereof, the method comprising administering to the subject an effective amount of a compound having a structure:

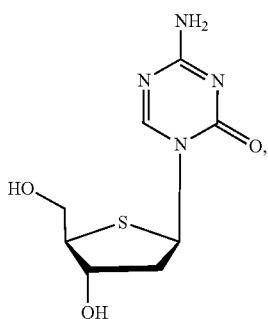 [SMILES: Nc1ncn([C@H]2C[C@@H](O)[C@@H](CO)S2)c(=O)n1]

wherein the effective amount is of from about 5 mg/m² to no more than about 70 mg/m² per 24 hour time period, thereby treating the blood cancer in the subject.

Also disclosed are methods of treating a blood cancer in a human subject in need thereof, the method comprising administering to the subject an effective amount of a compound having a structure:

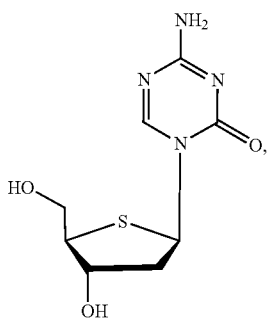 [SMILES: Nc1ncn([C@H]2C[C@@H](O)[C@@H](CO)S2)c(=O)n1]

wherein the effective amount is of from about 5 mg/m² to no more than about 70 mg/m² per 24 hour time period, thereby treating the blood cancer in the subject.

Also disclosed are methods of treating blood cancer, which includes administering a composition for oral administration, which includes Aza-T-dCyd of Formula 1 below, into a blood cancer patient at a dose of 5 to 70 mg/m²:

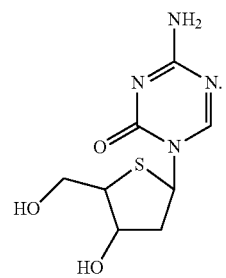

[Formula 1]

In various aspects, the administration is performed in a cycle, which includes: (a) administration of the composition for 4 to 6 days; (b) a 1- to 3-day break after the administration (a); (c) administration of the composition for 4 to 6 days after the break (b); and (d) an 8- to 10-day break after the administration (c).

In various aspects, the blood cancer may be any one or more selected from the group consisting of non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma.

Also disclosed are kits comprising an effective amount of a disclosed pharmaceutical composition, and one or more of: (a) at least one agent associated with the treatment of a disorder of uncontrolled cellular proliferation; (b) instructions for administering the composition in connection with treating a disorder of uncontrolled cellular proliferation; and (c) instructions for treating a disorder of uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The above and other objects, features and advantages of the present invention will become more apparent to those of ordinary skill in the art by describing in detail exemplary embodiments thereof with reference to the accompanying drawings.

Figure 1:
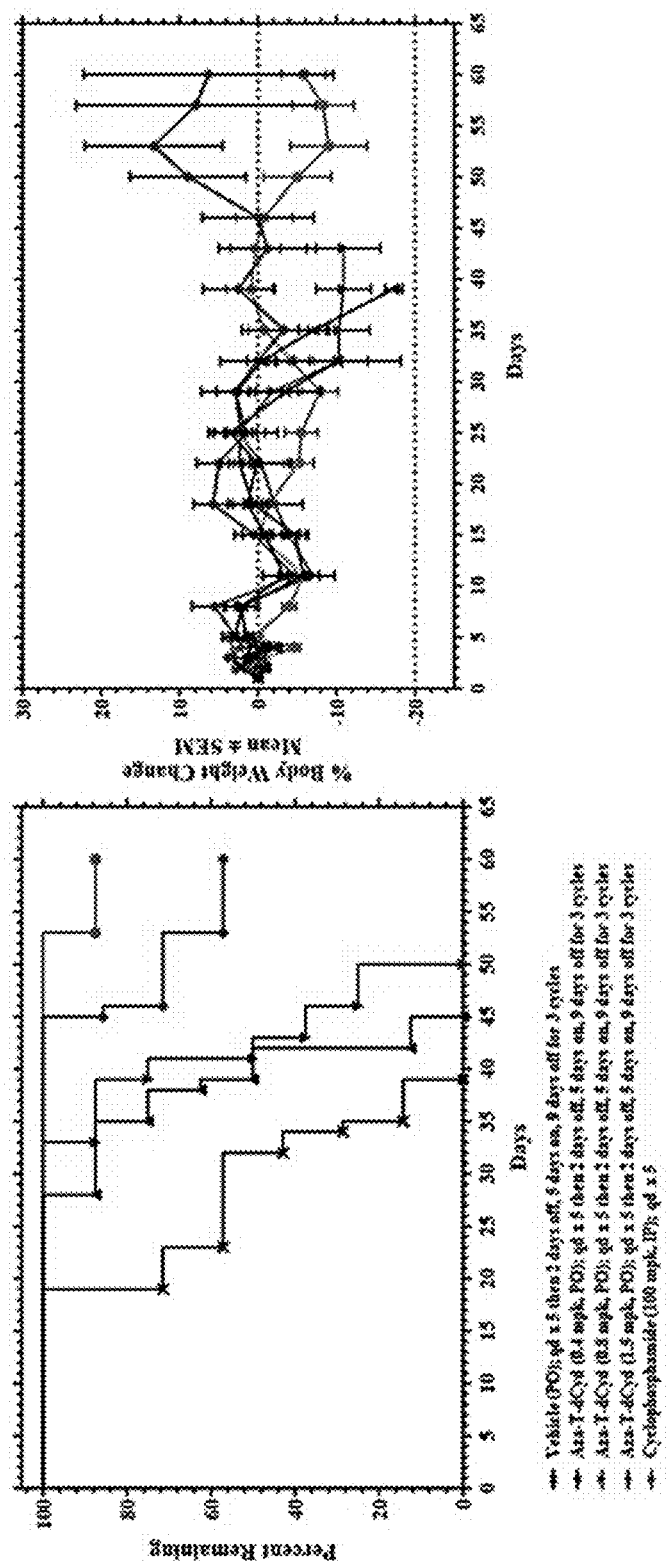
FIG. 1 shows representative data illustrating the comparison of the differences in survival rate and body weight per treated group (Aza-T-dCyd: 0.4, 0.8 or 1.5 mpk; cyclophosphamide: 100 mpk) in acute myelogenous leukemia (AML) experimental animal models.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein. As described above, as 4'-thio-5-aza-2'-deoxycytidine (Aza-T-dCyd) exhibits toxicity even at a small dose of 1.5 mpk in animal models with blood cancer such as ALL. As such, the use of Aza-T-dCyd for treatment of blood cancer has remained elusive, particularly when compared with other cytidine-based drugs such as decitabine and azacytidine.

Here, it is demonstrated that a significant anticancer effect can be obtained by administering Aza-T-dCyd to blood cancer mouse models at a dose of 1.4 to 2.6 mpk through oral administration (PO) for 5 days, a 2-day break, administration for 5 days, and a 9-day break. In view of these data, for human blood cancer, when Aza-T-dCyd was administered at 30 to 70 mg/m$^2$ through oral administration (PO) for 4 to 6 days, a 1- to 3-day break, administration for 4 to 6 days, and an 8- to 10-day break, a significantly anticancer effect is likely to be obtained.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an," and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$EC_{50}$," is intended to refer to the effective concentration of a substance (e.g., a compound or a drug) that is required for 50% inhibition of a biological process, or component of a process, including a protein, subunit, organelle, ribonucleoprotein, etc. In one aspect, an $EC_{50}$ can refer to the concentration of a substance that is required for 50% inhibition in vivo, as further defined elsewhere herein.

As used herein, "$EC_{90}$," is intended to refer to the effective concentration of a substance (e.g., a compound or a drug) that is required for 90% inhibition of a biological process, or component of a process, including a protein, subunit, organelle, ribonucleoprotein, etc. In one aspect, an $EC_{50}$ can refer to the concentration of a substance that is required for 90% inhibition in vivo, as further defined elsewhere herein.

As used herein, "$CC_{50}$," is intended to refer to the effective toxicity concentration of a substance (e.g., a compound or a drug) that is required for 50% inhibition of a biological process, or component of a process, including a protein, subunit, organelle, ribonucleoprotein, etc.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Pharmaceutical Compositions

In one aspect, disclosed are pharmaceutical compositions comprising a therapeutically effective amount of a compound having a structure:

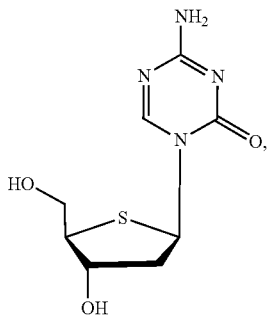 [SMILES: Nc1ncn([C@H]2C[C@@H](O)[C@@H](CO)S2)c(=O)n1]

and a pharmaceutically acceptable carrier, wherein the therapeutically effective amount is of from about 5 mg/m$^2$ to no more than about 70 mg/m$^2$, and wherein the pharmaceutical composition is formulated for oral administration.

In one aspect, disclosed are pharmaceutical compositions comprising a therapeutically effective amount of a compound having a structure:

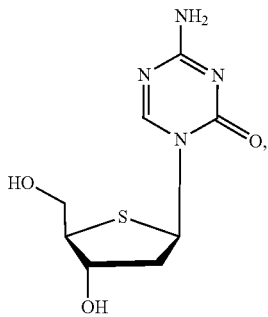 [SMILES: Nc1ncn([C@H]2C[C@@H](O)[C@@H](CO)S2)c(=O)n1]

and a pharmaceutically acceptable carrier, wherein the therapeutically effective amount is of from about 30 mg/m$^2$ to no more than about 70 mg/m$^2$, and wherein the pharmaceutical composition is formulated for oral administration.

In one aspect, disclosed are pharmaceutical compositions for treating blood cancer, which includes Aza-T-dCyd of Formula 1 below and is orally administered at 5 to 70 mg/m$^2$:

[Formula 1]

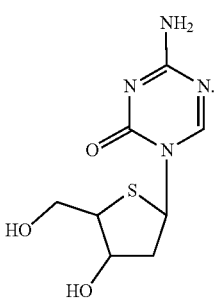

In one aspect, disclosed are pharmaceutical compositions for treating blood cancer, which includes Aza-T-dCyd of Formula 1 below and is orally administered at 30 to 70 mg/m$^2$:

[Formula 1]

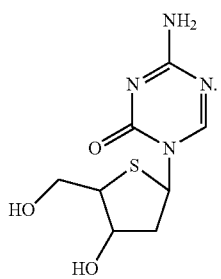

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

As would be readily appreciated by the skilled artisan, the nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol.

In various aspects, the pharmaceutical composition of the present invention is an oral formulation. For the formulation of the composition, the oral formulation may be prepared using one or more buffers (e.g., saline or PBS), an antioxidant, an antibacterial agent, a chelating agent (e.g., EDTA or glutathione), a filler, an expander, a binder, an adjuvant (e.g., aluminum hydroxide), a suspending agent, a thickening agent, a wetting agent, a disintegrant, a surfactant, a diluent, or an excipient.

Solid preparations for oral administration may include a tablet, a pill, a powder, a granule and a capsule, and may be prepared by mixing at least one excipient, for example, starch (including corn starch, wheat starch, rice starch, potato starch, etc.), calcium carbonate, sucrose, lactose, dextrose, sorbitol, mannitol, xylitol, erythritol, maltitol, cellulose, methyl cellulose, sodium carboxymethylcellulose, hydroxyproxymethyl-cellulose or gelatin with one or more compounds. For example, tablets or dragees may be obtained by combining an active ingredient with solid excipients, grinding the mixture, adding a suitable adjuvant and processing the resulting product into a granule mixture.

In addition, other than simple excipients, lubricants such as magnesium stearate, talc, etc. are also used. As a liquid preparation for oral administration, a suspending agent, a liquid for internal use, an emulsion or a syrup is used, and other than a commonly used simple diluent such as water or a liquid paraffin, various excipients, for example, a wetting agent, a sweetening agent, a fragrance and a preservative may be included. In addition, in some cases, crosslinked polyvinylpyrrolidone, agar, alginic acid or sodium alginate may be added as a disintegrant, and an anticoagulant, an aromatic, an emulsifier, a solubilizer, a dispersant, a flavoring agent, an antioxidant, a packaging agent, a pigment and a preservative may be further included.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Compositions containing a compound of the invention, and/or pharmaceutically acceptable salts thereof, can also be prepared in powder or liquid concentrate form.

In various aspects, the pharmaceutical composition may be orally administered at 5 to 35 mg/m$^2$. In various further aspects, the pharmaceutical composition may be orally administered at 5 to 10 mg/m$^2$. In various further aspects, the pharmaceutical composition may be orally administered at 35 to 45 mg/m$^2$. In various further aspects, the pharmaceutical composition may be orally administered at 45 to 55 mg/m$^2$. In various further aspects, the pharmaceutical composition may be orally administered at 55 to 66 mg/m$^2$.

In various aspects, the pharmaceutical composition may be orally administered at 5 mg/m$^2$ to no more than 35 mg/m$^2$ per 24 hour time period. In various further aspects, the pharmaceutical composition may be orally administered at 5 mg/m$^2$ to no more than 10 mg/m$^2$ per 24 hour time period. In various further aspects, the pharmaceutical composition may be orally administered at 35 mg/m$^2$ to no more than 45 mg/m$^2$ per 24 hour time period. In various further aspects, the pharmaceutical composition may be orally administered at 45 mg/m$^2$ to no more than 55 mg/m$^2$ per 24 hour time period. In various further aspects, the pharmaceutical composition may be orally administered at 55 mg/m$^2$ to no more than 66 mg/m$^2$ per 24 hour time period.

In various aspects, the administration may be performed in a cycle, which includes: (a) administration of the composition for 4 to 6 days; (b) a 1- to 3-day break after the administration (a); (c) administration of the composition for 4 to 6 days after the break (b); and (d) an 8- to 10-day break after the administration (c). In various further aspects, the administration is performed in a cycle, which includes: (a) administration of the composition for 5 days; (b) a 2-day break after the administration (a); (c) administration of the composition for 5 days after the break (b); and (d) a 9-day break after the administration (c).

In various aspects, the pharmaceutical composition is used to treat a blood cancer such as, for example, non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma. In various further aspects, the blood cancer is any one or more selected from the group consisting of MDS and AML.

It is understood that the disclosed compositions can be prepared from the disclosed compounds. It is also understood that the disclosed compositions can be employed in the disclosed methods of using.

C. Methods of Using the Compositions

The pharmaceutical compositions of the invention are useful in treating or controlling blood cancers, such as, for example, non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma. To treat or control the blood cancer, the compounds and pharmaceutical compositions comprising the compounds are administered to a subject in need thereof. The term "subject" does not denote a particular age or sex. Thus, adult and newborn subjects, as well as fetuses, whether male or female, are intended to be covered. Prior to administering the compositions, the subject can be diagnosed with a need for treatment of a blood cancer.

The compounds or compositions can be orally administered to the subject according to any method. Administration can be continuous or intermittent. A preparation can be administered therapeutically; that is, administered to treat an existing blood cancer. A preparation can also be administered prophylactically; that is, administered for prevention of a blood cancer.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Treatment Methods

The pharmaceutical compositions disclosed herein are useful for treating or controlling blood cancers, such as, for example, non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma. Thus, provided is a method comprising administering a pharmaceutical composition comprising a therapeutically effective amount of a disclosed compound to a subject. In a further aspect, the method can be a method for treating a blood cancer.

A. Treating Blood Cancer

In one aspect, disclosed are methods of treating a blood cancer in a human subject in need thereof, the method comprising administering to the subject an effective amount of a compound having a structure:

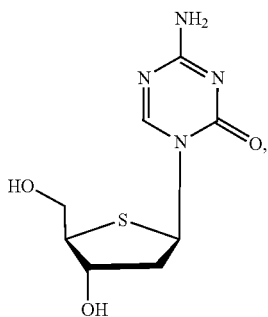 [SMILES: Nc1ncn([C@H]2C[C@@H](O)[C@@H](CO)S2)c(=O)n1]

wherein the effective amount is of from about 5 mg/m² to no more than about 70 mg/m² per 24 hour time period, thereby treating the blood cancer in the subject.

In one aspect, disclosed are methods of treating a blood cancer in a human subject in need thereof, the method comprising administering to the subject an effective amount of a compound having a structure:

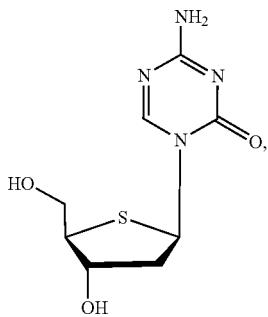 [SMILES: Nc1ncn([C@H]2C[C@@H](O)[C@@H](CO)S2)c(=O)n1]

wherein the effective amount is of from about 30 mg/m² to no more than about 70 mg/m² per 24 hour time period, thereby treating the blood cancer in the subject.

In one aspect, disclosed are methods of treating blood cancer, which includes administering a composition for oral administration, which includes Aza-T-dCyd of Formula 1 below, into a blood cancer patient at a dose of 5 to 70 mg/m²:

[Formula 1]

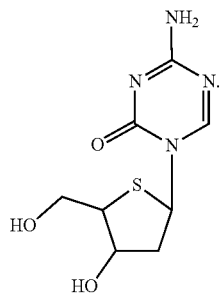

In one aspect, disclosed are methods of treating blood cancer, which includes administering a composition for oral administration, which includes Aza-T-dCyd of Formula 1 below, into a blood cancer patient at a dose of 30 to 70 mg/m²:

[Formula 1]

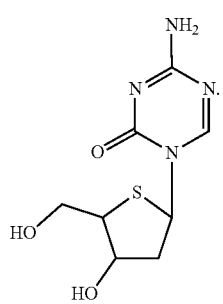

The "oral administration" is the same as the concept used in the pharmaceutical composition, and the description thereof will be replaced by the above description.

In various aspects, the composition for oral administration may be administered at 5 to 35 mg/m². In various further aspects, the composition for oral administration may be administered at 5 to 10 mg/m². In various further aspects, the composition for oral administration may be administered at 35 to 45 mg/m². In various further aspects, the composition for oral administration may be administered at 45 to 55 mg/m². In various further aspects, the composition for oral administration may be administered at 55 to 66 mg/m².

In various aspects, the effective amount is of from about 5 mg/m² to no more than about 35 mg/m² per 24 hour time period. In various further aspects, the effective amount is of from about 5 mg/m² to no more than about 10 mg/m² per 24 hour time period. In various further aspects, the effective amount is of from about 35 mg/m² to no more than about 45 mg/m² per 24 hour time period. In various further aspects, the effective amount is of from about 45 mg/m² to no more than about 55 mg/m² per 24 hour time period. In various further aspects, the effective amount is of from about 55 mg/m² to no more than about 66 mg/m² per 24 hour time period.

In various aspects, the effective amount is a therapeutically effective amount. In various further aspects, the effective amount is a prophylactically effective amount.

In various aspects, the effective amount is administered in a single dose. In various further aspects, the effective amount is administered via a plurality of doses. In various further aspects, the effective amount is administered via two or three doses. In various further aspects, the effective amount is administered via two doses. In various further aspects, the effective amount is administered via three doses.

In various aspects, the subject has been diagnosed with a need for treatment of blood cancer prior to the administering step. In various further aspects, the method further comprises the step of identifying a subject in need of treatment of blood cancer.

In various aspects, administering is repeated administration.

In various aspects, administering is for a time period of from about 4 days to about 6 days. In various further aspects, administering is for a time period of from about 4 days to about 5 days. In various further aspects, administering is for a time period of from about 5 days to about 6 days. In various further aspects, administering is for a time period of about 4 days. In various further aspects, administering is for a time period of about 5 days. In various further aspects, administering is for a time period of about 6 days.

In various aspects, administering is via a treatment cycle. In a further aspect, administering is via a course of treatment comprising a plurality of treatment cycles and a plurality of rest periods.

In a further aspects, each treatment cycle includes administering the effective amount of the compound for a time period of from about 4 days to about 6 days. In a still further aspect, each treatment cycle includes administering the effective amount of the compound for a time period of from about 4 days to about 5 days. In yet a further aspect, each treatment cycle includes administering the effective amount of the compound for a time period of from about 5 days to about 6 days. In an even further aspect, each treatment cycle includes administering the effective amount of the compound for a time period of about 4 days. In a still further aspect, each treatment cycle includes administering the effective amount of the compound for a time period of about 5 days. In yet a further aspect, each treatment cycle includes administering the effective amount of the compound for a time period of about 6 days.

In a further aspect, each rest period includes abstaining from administering the compound for a time period of from about 1 day to about 10 days. In a still further aspect, each rest period includes abstaining from administering the compound for a time period of from about 1 day to about 8 days. In yet a further aspect, each rest period includes abstaining from administering the compound for a time period of from about 1 day to about 6 days. In an even further aspect, each rest period includes abstaining from administering the compound for a time period of from about 1 day to about 4 days. In a still further aspect, each rest period includes abstaining from administering the compound for a time period of from about 1 day to about 2 days. In yet a further aspect, each rest period includes abstaining from administering the compound for a time period of from about 2 days to about 10 days. In an even further aspect, each rest period includes abstaining from administering the compound for a time period of from about 4 days to about 10 days. In a still further aspect, each rest period includes abstaining from administering the compound for a time period of from about 6 days to about 10 days. In yet a further aspect, each rest period includes abstaining from administering the compound for a time period of from about 8 days to about 10 days.

In various aspects, administering is via a course of treatment comprising: (a) a first treatment cycle that includes administering the effective amount of the compound for a time period of from about 4 days to about 6 days; (b) a first rest period that includes abstaining from administering the compound for a time period of from about 1 day to about 3 days; (c) a second treatment cycle that includes administering the effective amount of the compound for a time period of from about 4 days to about 6 days; and (d) a second rest period that includes abstaining from administering the compound for a time period of at least about 8 days.

In various aspects, the administration is performed in a cycle, which includes: (a) administration of the composition for 4 to 6 days; (b) a 1- to 3-day break after the administration (a); (c) administration of the composition for 4 to 6 days after the break (b); and (d) an 8- to 10-day break after the administration (c). In various further aspects, the administration is performed in a cycle, which includes: (a) administration of the composition for 5 days; (b) a 2-day break after the administration (a); (c) administration of the composition for 5 days after the break (b); and (d) a 9-day break after the administration (c).

In various aspects, administering is via a course of treatment comprising: (a) a first treatment cycle that includes administering the effective amount of the compound once per day for a time period of about 5 days; (b) a first rest period that includes abstaining from administering the compound for a time period of about 2 days; (c) a second treatment cycle that includes administering the effective amount of the compound once per day for a time period of about 5 days; and (d) a second rest period that includes abstaining from administering the compound for a time period of at least about 9 days.

In various aspects, the effective amount is administered in a single dose. In various further aspects, the effective amount is administered via a plurality of doses. In various further aspects, the effective amount is administered via a single dose on some days and via a plurality of doses on other days.

In various aspects, the blood cancer may be any one or more selected from the group consisting of non-Hodgkin's lymphoma, Hodgkin's lymphoma, multiple myeloma, leukemia, lymphoma, MDS, acute lymphocytic leukemia, AML, chronic lymphocytic leukemia, chronic myeloid leukemia and solitary myeloma. In various further aspects, the blood cancer is any one or more selected from the group consisting of MDS and AML.

In various aspects, the method further comprises the step of administering an effective amount of at least one chemotherapeutic agent. Examples of chemotherapeutic agents include, but are not limited to, alkylating agents, antimetabolite agents, antineoplastic antibiotic agents, mitotic inhibitor agents, and mTor inhibitor agents.

In a further aspect, the composition and the chemotherapeutic agent are administered sequentially. In a still further aspect, the composition and the chemotherapeutic agent are administered simultaneously.

In a further aspect, the composition and the chemotherapeutic agent are co-formulated. In a still further aspect, the composition and the chemotherapeutic agent are co-packaged.

2. Use of Compounds and Compositions

In one aspect, the invention relates to the use of a disclosed composition. In a further aspect, a use relates to the manufacture of a medicament for the treatment of a blood cancer in a subject.

In a further aspect, the use relates to a process for preparing a disclosed pharmaceutical composition for use as a medicament.

In a further aspect, the use relates to a process for preparing a disclosed pharmaceutical composition, wherein a pharmaceutically acceptable carrier is intimately mixed with a therapeutically effective amount of the compound.

In various aspects, the use relates to a treatment of a blood cancer in a subject. In one aspect, the use is characterized in that the subject is a human. In one aspect, the use is characterized in that the blood cancer is non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, or solitary myeloma.

In a further aspect, the use relates to the manufacture of a medicament for the treatment of a blood cancer in a subject. In one aspect, the use is characterized in that the blood cancer is non-Hodgkin's lymphoma, Hodgkin's lymphoma, multiple myeloma, leukemia, lymphoma, myelodysplastic syndrome, acute lymphocytic leukemia, acute myelogenous leukemia, chronic lymphocytic leukemia, chronic myeloid leukemia, or solitary myeloma.

3. Manufacture of a Medicament

In one aspect, the invention relates to a method for the manufacture of a medicament for treating a blood cancer in a human subject having the blood cancer, the method comprising combining a therapeutically effective amount of a disclosed compound with a pharmaceutically acceptable carrier or diluent.

As regards these applications, the present method includes the administration to a human of a therapeutically effective amount of the composition. The dose administered to a human, in the context of the present invention, should be sufficient to affect a therapeutic response in the human over a reasonable time frame. One skilled in the art will recognize that dosage will depend upon a variety of factors including the condition of the human and the body weight of the human.

The total amount of the composition of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the composition and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound, or a pharmaceutically acceptable salt, solvate, or polymorph thereof, with a pharmaceutically acceptable carrier or diluent.

4. Kits

In one aspect, disclosed are kits comprising an effective amount of a disclosed pharmaceutical composition, and one or more of: (a) at least one agent associated with the treatment of a disorder of uncontrolled cellular proliferation; (b) instructions for administering the composition in connection with treating a disorder of uncontrolled cellular proliferation; and (c) instructions for treating a disorder of uncontrolled cellular proliferation.

In a further aspect, the agent is a chemotherapeutic agent. Examples of chemotherapeutic agents include, but are not limited to, alkylating agents, antimetabolite agents, antineoplastic antibiotic agents, mitotic inhibitor agents, and mTor inhibitor agents.

In a further aspect, the chemotherapeutic agent is an alkylating agent. Examples of alkylating agents include, but are not limited to carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt thereof.

In a further aspect, the chemotherapeutic agent is an antimetabolite agent. Examples of antimetabolite agents include, but are not limited to, gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

In a further aspect, the chemotherapeutic agent is an antineoplastic antibiotic agent. Examples of antineoplastic antibiotic agents include, but are not limited to doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

In a further aspect, the chemotherapeutic agent is a mitotic inhibitor agent. Examples of mitotic inhibitor agents include, but are not limited to, irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof.

In a further aspect, the chemotherapeutic agent is an mTor inhibitor agent. Examples of mTor inhibitor agents include, but are not limited to, everolimus, siroliumus, and temsirolimus, or a pharmaceutically acceptable salt, hydrate, solvate, or polymorph thereof.

In various aspects, the pharmaceutical composition and the agent are co-packaged. In various further aspects, the pharmaceutical composition and the agent are co-formulated.

In various further aspects, the pharmaceutical composition and the agent are administered sequentially. In various further aspects, the pharmaceutical composition and the agent are administered simultaneously.

In various aspects, the disorder of uncontrolled cellular proliferation is a cancer. In various further aspects, the cancer is a blood cancer.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter, which is broadly contemplated by the present invention. It is further understood that the scope of the present invention fully encompasses other embodiments that may become obvious to those skilled in the art and that the scope of the present invention is accordingly not limited.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Determination of Dose oF Aza-T-dCyd

In the case of elderly patients who cannot receive bone marrow transplants, that is, the main targets of decitabine and azacytidine, toxicity in the bone marrow becomes the limit dose that determines a dose for administration, and, thus, the maximum dose that enables safe administration was to be determined.

After 0.4 to 2.5 mpk of Aza-T-dCyd was administered to a normal mouse in one cycle (oral administration (PO) for 5 days, a 2-day break, administration for 5 days, and a 9-day break), the bone marrow was extracted, and then the viability and composition change of each cell constituting the bone marrow were observed.

As a result, it can be confirmed that, up to 2.0 mpk, there was no significant change in the viability and composition of each cell in the bone marrow. 2.0 to 2.5 mpk is the range overlapping the dose of 1.5 mpk, which was reported to exhibit high toxicity in the ALL model, and, thus, the administration at a dose in this range was expected to require care, but did not have a significant effect on toxicity to the bone marrow, so the reported toxicity was determined to be disease-specific rather than general. However, at 2.5 mpk, a significant change in the bone marrow started to be observed, and when efficacy was confirmed at a lower dose than 2.5 mpk, the relevant dose was determined as a non-preferable dose.

As a result of the one-cycle administration of Aza-T-dCyd, as described above, to a xenograft model to which Molm13 AML cells were subcutaneously transplanted, it can be confirmed that, when 1.5 or 2.5 mpk of Aza-T-dCyd was administered PO, excellent anticancer efficacy close to tumor regression was exhibited.

As a result of three cycles of the PO administration of 0.4 to 2.5 mpk of Aza-T-dCyd to a systemic AML model in which MV4-11 AML cells were transplanted into the bone marrow, it was confirmed that the administration of 2.0 mpk of Aza-T-dCyd showed very excellent survival improvement, and clinical observations including mouse body weight also remained in the normal range. The PO administration of 2.5 mpk of Aza-T-dCyd led to the death of some subjects, and in the case of the PO administration of 1.5 mpk of Aza-T-dCyd, an efficacy which did not reach that of the PO administration of 2.0 to 2.5 mpk of Aza-T-dCyd was shown (FIG. 1).

As a result of PK measurement at 2.0 mpk PO, it was confirmed that the total area under curve (AUC) is changed at a maximum range of approximately 25% (±12.5%), confirming that the administration dose range that covers the changes is 1.4 to 2.6 mpk PO.

Figure 2:
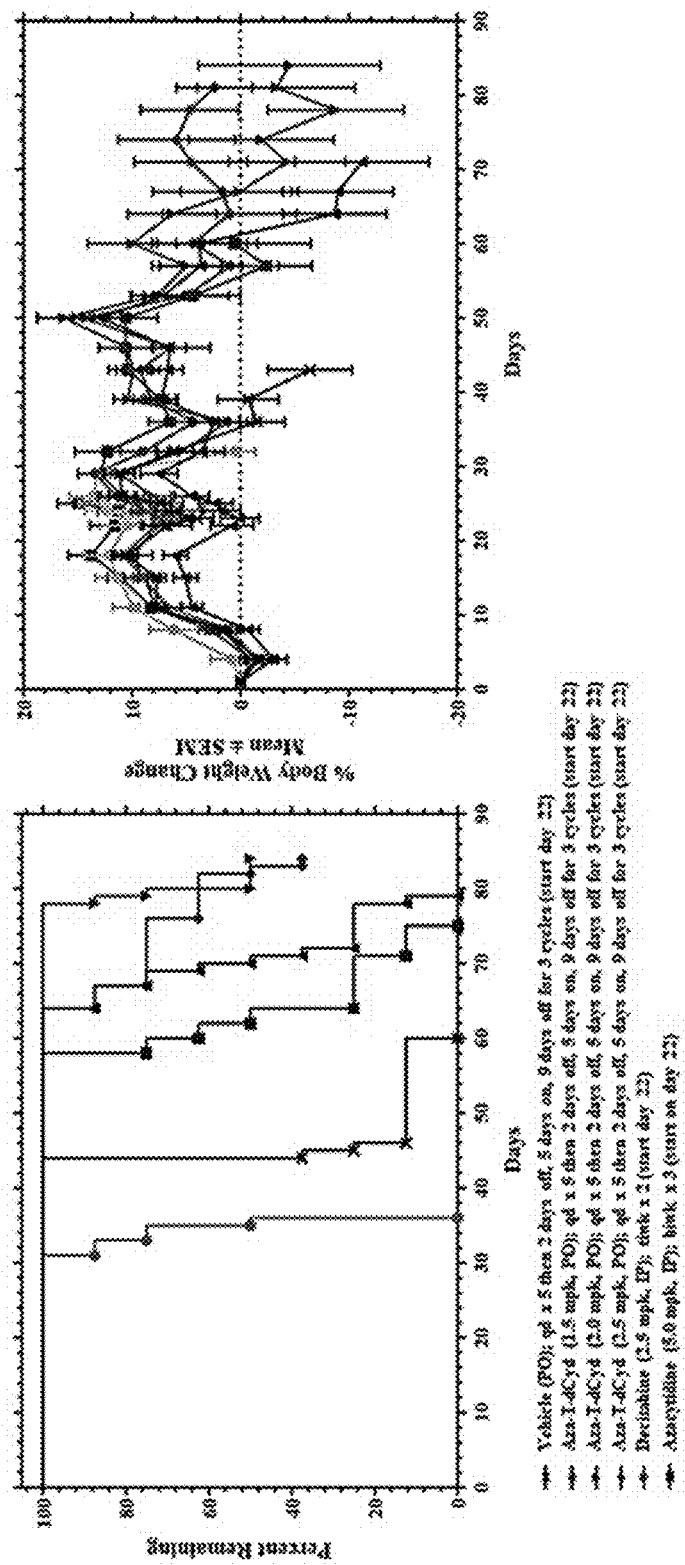
FIG. 2 shows representative data illustrating the comparison of the differences in survival rate and body weight per treated group (Aza-T-dCyd: 1.5, 2.0 or 2.5 mpk; Decitabine: 2.5 mpk; Azacytidine: 5.0 mpk) in AML experimental animal models.

As a result of administering Aza-T-dCyd to a systemic AML model in which MV4-11 AML cells were transplanted into the bone marrow in one cycle of 1.5, 2.0, or 2.5 mpk PO, and administering decitabine and azacytidine at optimal doses as controls, it can be confirmed that decitabine did not show survival improvement, and azacytidine showed a limited level of survival improvement, whereas the administration of 2.0 mpk of Aza-T-dCyd showed very excellent survival improvement, and clinical observations including body weight were also confirmed to stay in the normal range (FIG. 2).

2. Application of Aza-T-dCyd in Elderly Patient

Blood analysis was performed by collecting blood samples in the above-described experimental process to confirm whether the dose of Aza-T-dCyd determined in Example 1 above can be used in elderly AML patients.

As a result, it was confirmed that there was no change in major parameters such as white blood cell (WBC), neutrophil, platelet, or red blood cell (RBC) levels. However, in the decitabine-treated group, all subjects had already died before the collection of blood samples, whereas in the azacytidine-treated group, subjects were alive until the first collection of blood samples but showed severe neutropenia, and some of them showed a serious tumor burden at the time of the second collection of blood samples.

Figure 3:
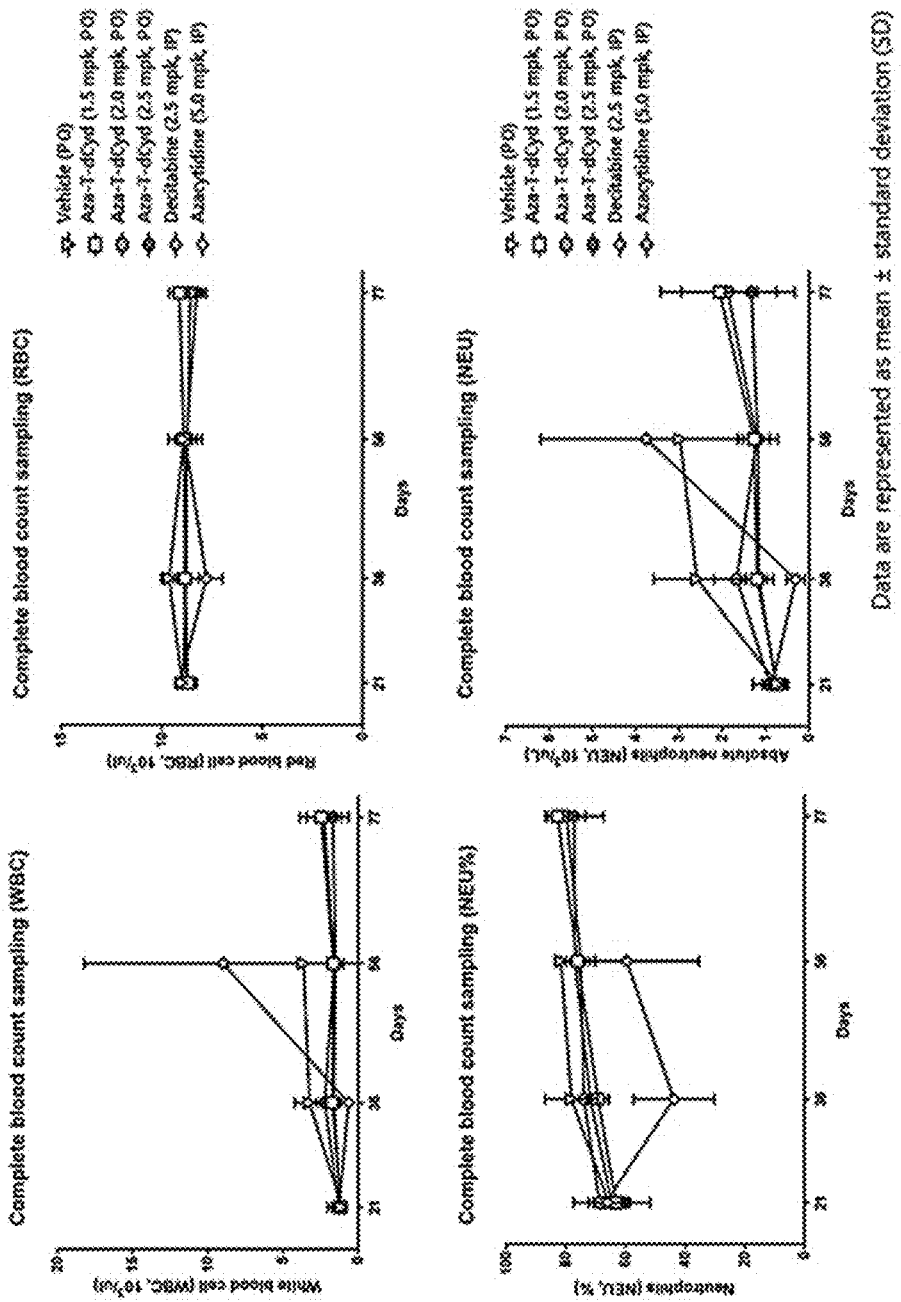
FIG. 3 shows representative data illustrating the comparison of levels of complete blood count (CBC) sampling per treated group (Aza-T-dCyd: 1.5, 2.0 or 2.5 mpk; Decitabine: 2.5 mpk; Azacytidine: 5.0 mpk) in AML experimental animal models (WBC: white blood cell, RBC: red blood cell, NEU: neutrophil).
Figure 4:
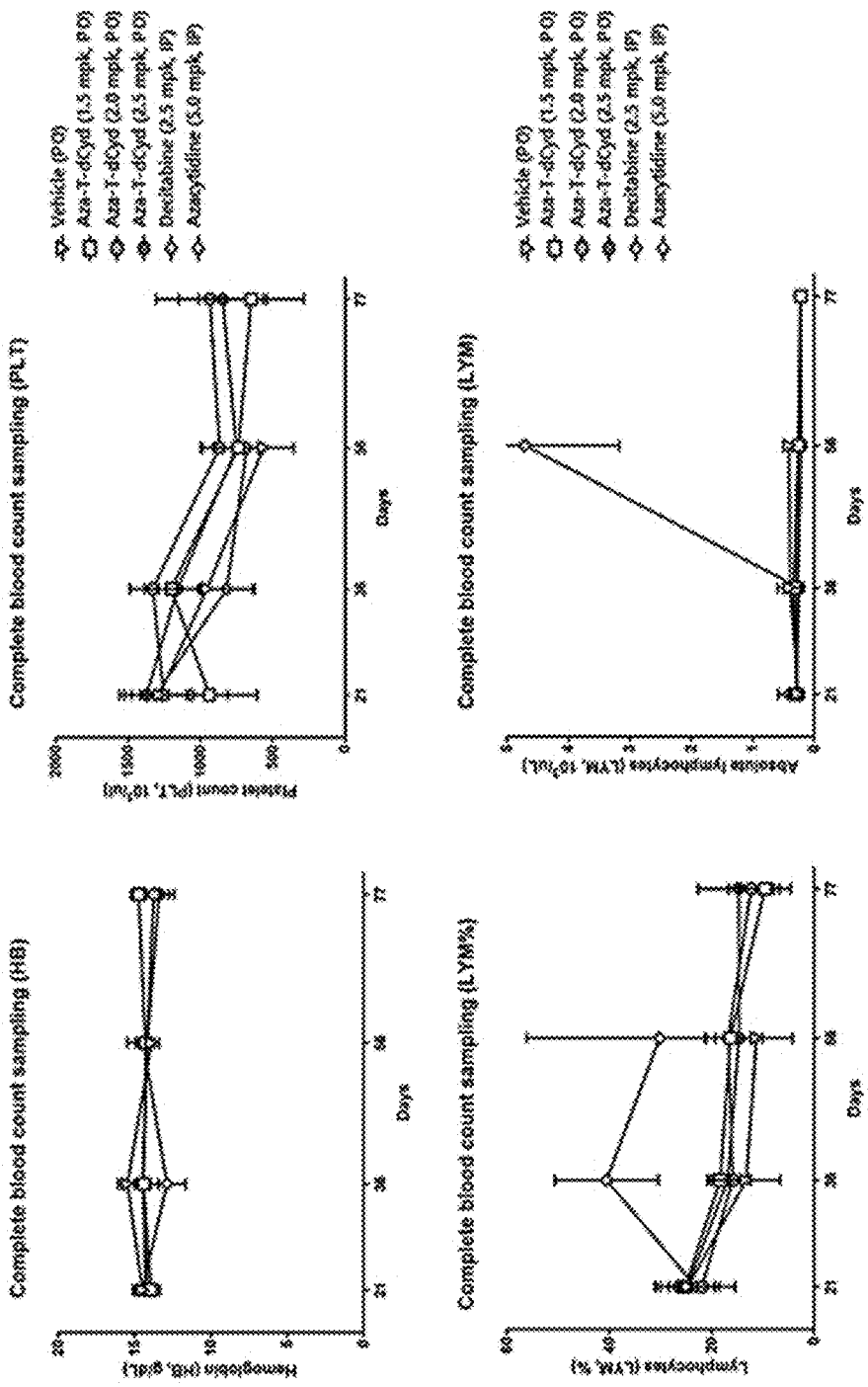
FIG. 4 shows representative data illustrating the comparison of levels of CBC sampling per treated group (Aza-T-dCyd: 1.5, 2.0 or 2.5 mpk; Decitabine: 2.5 mpk; Azacytidine: 5.0 mpk) in AML experimental animal models (HB: hemoglobin, PLT: platelet, LYM: lymphocyte).
Figure 5:
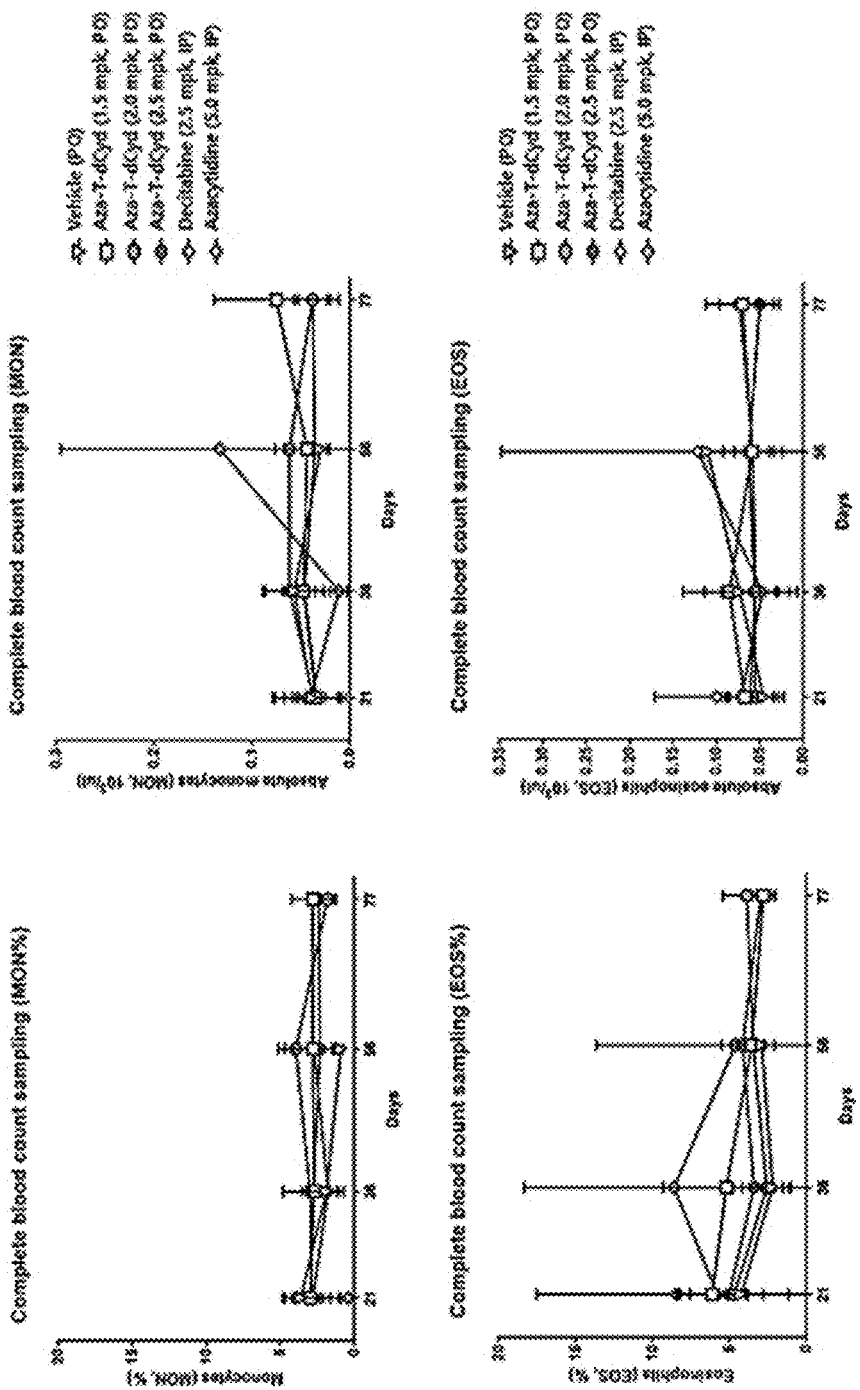
FIG. 5 shows representative data illustrating the comparison of levels of CBC sampling per treated group (Aza-T-dCyd: 1.5, 2.0 or 2.5 mpk; Decitabine: 2.5 mpk; Azacytidine: 5.0 mpk) in AML experimental animal models (MON: monocyte, EOS: eosinophil).
Figure 6:
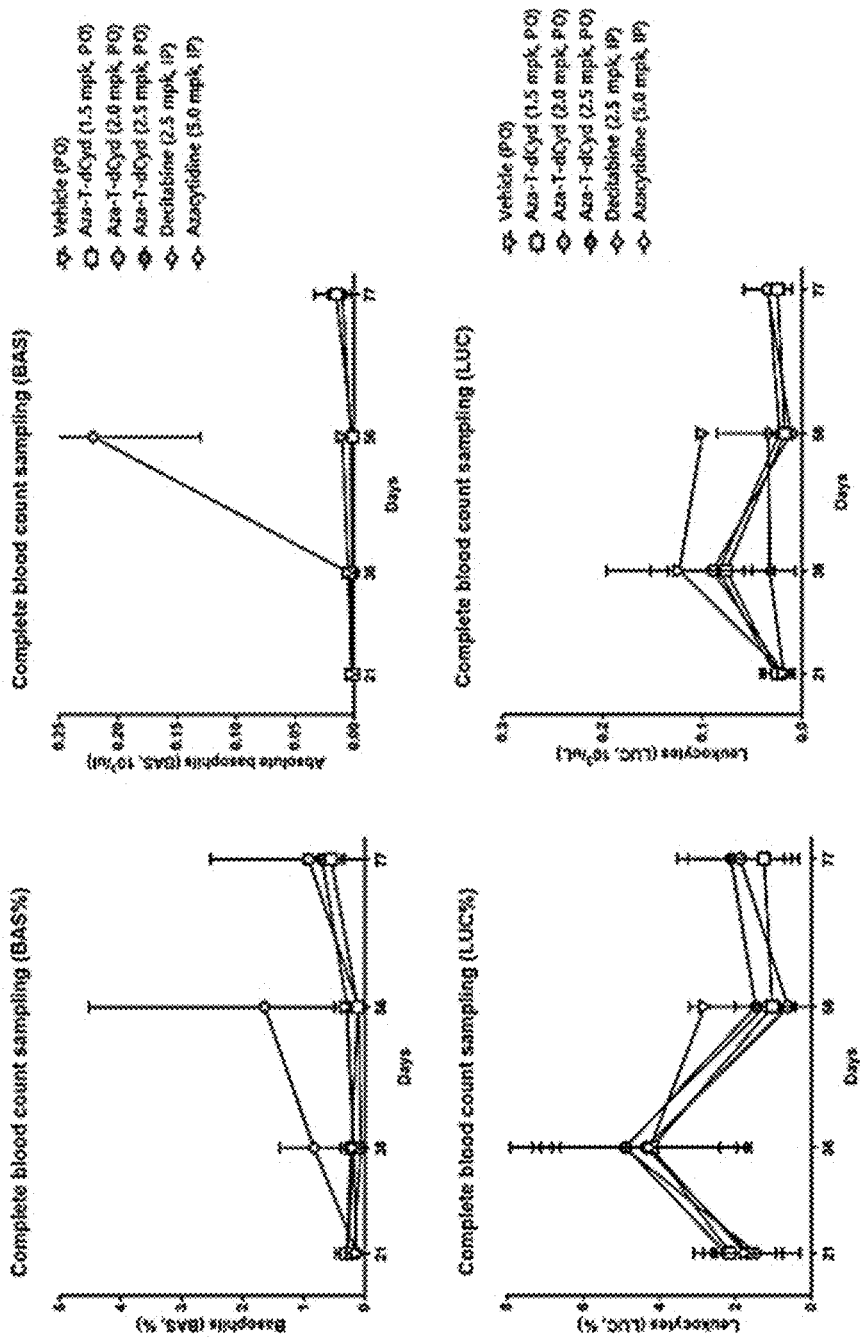
FIG. 6 shows representative data illustrating the comparison of levels of CBC sampling per treated group (Aza-T-dCyd: 1.5, 2.0 or 2.5 mpk; Decitabine: 2.5 mpk; Azacytidine: 5.0 mpk) in AML experimental animal models (BAS: basophil, LUC: large unstained cell).

That is, it was confirmed that the optimal therapeutic composition according to the present invention (a composition including 1.4 to 2.6 mpk of Aza-T-dCyd as an active ingredient based on a mouse) showed excellent therapeutic efficacy against MDS/AML, which had not yet been confirmed in conventional research on Aza-T-dCyd, and the efficacy was at an unexpected level, compared to conventional commercially-available drugs such as decitabine and azacytidine (FIG. 3).

Figure 7:
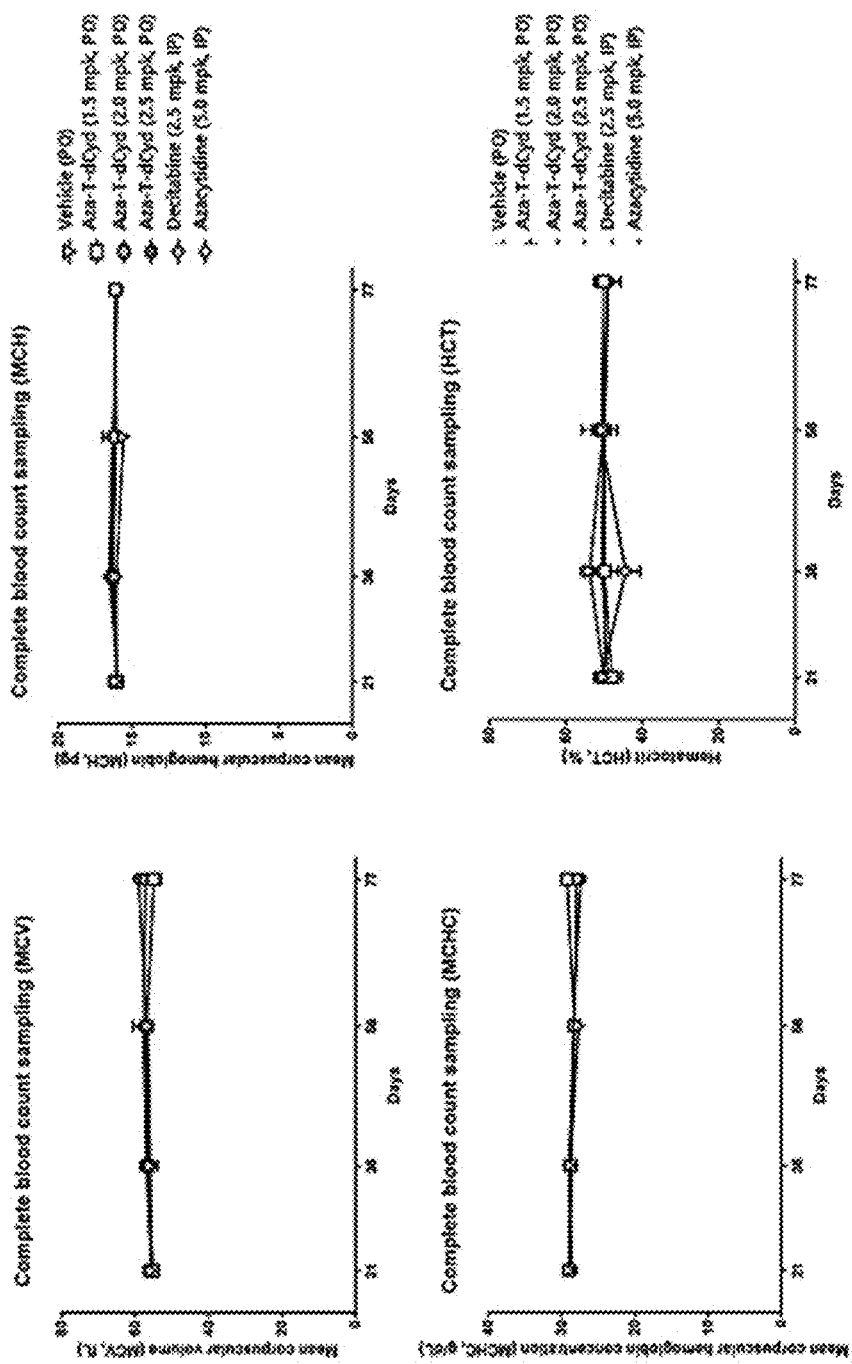
FIG. 7 shows representative data illustrating the comparison of levels of CBC sampling per treated group (Aza-T-dCyd: 1.5, 2.0 or 2.5 mpk; Decitabine: 2.5 mpk; Azacytidine: 5.0 mpk) in AML experimental animal models (MCV: mean corpuscular volume, MCH: mean corpuscular hemoglobin, MCHC: mean corpuscular hemoglobin concentration, HCT: hematocrit).

3. Determination of Dose of Aza-T-dCyd to Human a. Human Parameter Prediction by Interspecies Scaling A dose to a human was determined based on PK data for mice, rats, or dogs to convert the dose of Aza-T-dCyd determined in Example 1 above into the dose thereof to a human. PK parameters were scaled allometrically and used to extrapolate the PK in a 70 kg human. Details are described in the next section. The predicted human PK parameters are shown below in Table 1. See also FIG. 3 and FIG. 7.

TABLE 1

| Parameters | Description (Units) | Predicted Value |
|---|---|---|
| CL | Clearance (L/h) | 8.95 |
| $V_c$ | Central volume (L) = V2 | 29.50 |
| $V_p$ | Peripheral volume (L) = V3 | 12.92 |
| Q | Intercompartmental clearance (L/h) | 250.52 |
| $K_a$ | The first-order absorption rate constant (1/h) | 2.8 |
| F | Absolute bioavailability | 0.6 | b. Allometric Scaling for Cl, Vc, Vp & Q

Figure 8:
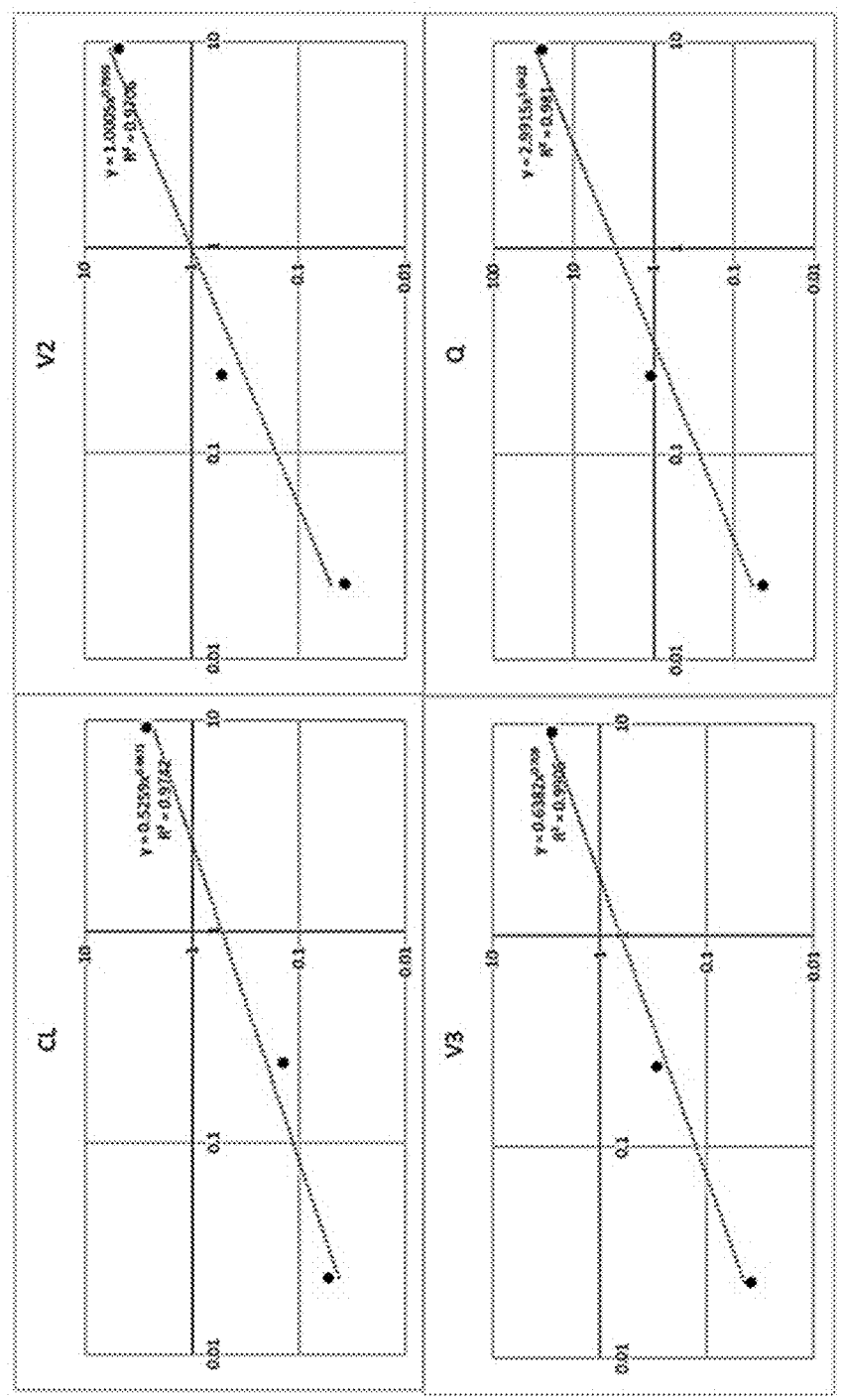
FIG. 8 shows representative data illustrating the relative scaling results between species for clearance (CL), central volume (V2), peripheral volume (V3) and intercompartmental clearance (Q).
Figure 9:
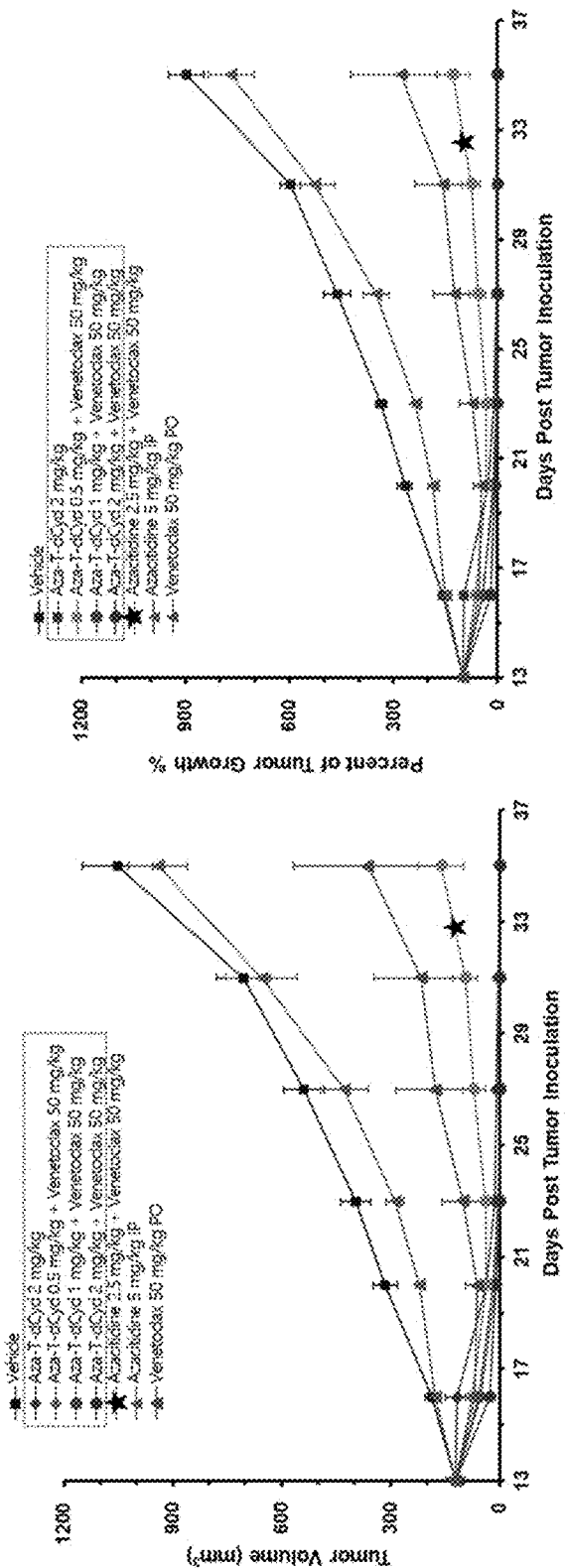
FIG. 9 shows representative data illustrating the comparison of the tumor volume and percent of tumor growth (%) per treated groups (Aza-T-dCyd: 0.5, 1.0 or 2.0 mpk; Venetoclax: 50 mpk; and Azacytidine: 2.5 or 5.0 mpk) in AML experimental animal models.

Simple allometric scaling, was used to predict CL, Vc, Vp, and Q. Y is PK parameter, BW is body weight, a is the allometric coefficient, and b is the allometric exponent. Final PK parameters, CL, Vc, Vp, and Q, were extrapolated based on the best-fit-lines (FIG. 8).

c. Prediction of Other Human Pk Parameters: Ka, F

The average absorption rate constant (Ka) and bioavailability (F) from three species were approximately 2.63 h$^{-1}$ and 0.54, respectively. The $T_{max}$ range of the three species was 0.25-2 hours. If it is assumed that $T_{max}$ in a human is 1 hour, Ka is estimated to be 2.8 h$^{-1}$, which is not different from the average Ka from the three species. The human F calculated by the equation reported in literature was about 0.65 (from mouse), 0.59 (from rat), or 0.66 (from dog). See Musther et al. (2014) *European Journal of Pharmaceutical Sciences* 57: 280-291. In consideration of the above results, human Ka and F were set to 2.8 h$^{-1}$ and 0.6, respectively. Table 2 represents Reference table for prediction of human bioavailability (From Mouse: F_human=0.507*50.65+

39.478=65.16; From Rat: F_human=0.544*43.2+35.759=59.26; From Dog: F_human=0.580*68.7+26.433=66.28).

d. Simulation of Human Pk Using Decitabine Pk Parameters

The predicted human decitabine CL using animal decitabine IV data was approximately 7 L/h, which was significantly different from the decitabine clearance (152 L/h) reported in literature. This was probably due to species differences in cytidine deaminase. NCA parameters of Aza-T-dCyd and decitabine in animals were similar (Table 2). Therefore, human simulations were performed using decitabine PK parameters (CL, Vc, Vp, Q) instead of human PK parameters predicted by interspecies scaling. For absorption rate constant (Ka) and bioavailability (F), animal parameters were used. The PK parameters used in this (human) simulation are shown in Table 3.

4. Combination Treatment of Aza-T-dycd and Venetoclax

After 2.0 mpk of Aza-T-dCyd was administered in one cycle (PO administration for 5 days, a 2-day break, PO administration for 5 days, and a 9-day break); or 0.5, 1.0 or 2.0 mpk of Aza-T-dCyd in combination with 50 mpk of Venetoclax were administered in one cycle (PO administration for 5 days, and a 2-day break for 3 weeks) to a xenograft AML model in which MV4-11 AML cells were subcutaneously transplanted, then anti-cancer effects were observed. 5.0 mpk of Azacitidine alone; or 2.5 mpk of Azacitidine in combination of 50 mpk of Venetoclax were intraperitoneal (IP) administered as a control.

As a result, the administration of 2.0 mpk of Aza-T-dCyd alone showed very excellent anti-cancer effects. Also, the administration of 0.5 mpk (15 mg) of Aza-T-dCyd in combination with Venetoclax showed very excellent anti-cancer effects similar to the administration of 2.0 mpk of Aza-T-

TABLE 2

| Species | mg/kg | CL (L/h/kg) Aza-T-dCyd | CL (L/h/kg) Decitabine | $t_{1/2}$ (h) Aza-T-dCyd | $t_{1/2}$ (h) Decitabine | C0 (ng/mL) Aza-T-dCyd | C0 (ng/mL) Decitabine | AUCinf (ng*h/mL) Aza-T-dCyd | AUCinf (ng*h/mL) Decitabine | Vss (L/kg) Aza-T-dCyd | Vss (L/kg) Decitabine |
|---|---|---|---|---|---|---|---|---|---|---|---|
| Mouse | 1 | 2.54 | 3.75 | 0.6 | 0.4 | 616.0 | 578.8 | 405.5 | 267.9 | 1.9 | 1.7 |
| Rat | 1 | 0.53 | 0.42 | 5.01 | 3.71 | 562 | 504 | 1900 | 2372 | 3.53 | 2.16 |
| Dog | 0.33 | 0.30 | 0.31 | 2.25 | 1.19 | 586 | 746 | 1128 | 1076 | 0.81 | 0.476 |

TABLE 3

| Parameters | Description (Units) | Value |
|---|---|---|
| CL | Clearance (L/h) | 152 |
| $V_c$ | Central volume (L) = V2 | 32 |
| $V_p$ | Peripheral volume (L) = V3 | 40 |
| Q | Intercompartmental clearance (L/h) | 23 |
| $K_a$ | The first-order absorption rate constant (1/h) | 2.8 |
| F | Absolute bioavailability | 0.6 |

As a result, it was confirmed that when the dose of Aza-T-dCyd was 5 mg/m² to 70 mg/m², an anticancer effect on blood cancer was exhibited. Without wishing to be bound by theory, this is excellent efficacy at a level that is impossible to reach by the same family of cytidine-based drugs such as decitabine or azacytidine, which was conventionally used, and according to conventional reports on Aza-T-dCyd, the level corresponds to a dose of a level expected to have toxicity. Table 4 shows AUC values measured from mouse PK results and numerical values (calculated values) simulated with a dose for humans.

TABLE 4

| mpk | AUC values (ng*h/mL) | Human prediction (mg) | Human prediction (mg/m²) |
|---|---|---|---|
| 0.07 | 11.3 | 2 | 1.25 |
| 0.13 | 19.33 | 4 | 2.5 |
| 0.27 | 38.06 | 8 | 5 |
| 0.4 | 55.4 | 10.12 | 6.32 |
| 0.8 | 108.9 | 20.25 | 12.65 |
| 1.0 | 135.7 | 30.26 | 18.91 |
| 1.4 | 183.2 | 48 | 30 |
| 1.5 | 202.6 | 55.23 | 34.51 |
| 2.0 | 269.5 | 80.2 | 50.12 |
| 2.5 | 336.4 | 105.18 | 65.73 |
| 2.6 | 354.6 | 112 | 70 |
| 3.0 | 403.3 | 130.15 | 81.34 |
| 10 | 1339.9 | 479.78 | 299.86 | dCyd alone. However, the administration of Azacitidine alone did not show the decrease of tumor volume, and the administration of Venetoclax alone showed a limited level of tumor regression.

Without wishing to be bound by theory, a method of treating blood cancer using 4'-thio-5-aza-2'-deoxycytidine (Aza-T-dCyd) and a pharmaceutical composition for treating blood cancer, which includes Aza-T-dCyd, according to the present invention can provide a significant therapeutic effect on blood cancer without toxicity in a blood cancer mouse model or a human even at a dose of Aza-T-dCyd previously known to be toxic.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of treating a blood cancer in a human subject in need thereof, the method comprising orally administering to the subject an effective amount of a compound having a structure:

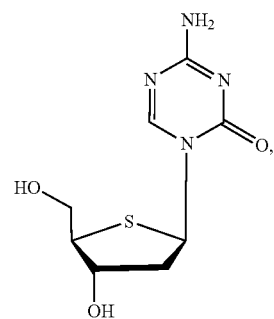

wherein the effective amount is of from about 1.25 mg/m² to no more than about 34.51 mg/m² per 24 hour time period, wherein the blood cancer is multiple myeloma, leukemia, myelodysplastic syndrome, or solitary myeloma, and wherein administering is via a course of treatment comprising:
(a) a first treatment cycle that includes administering the effective amount of the compound for a time period of from about 4 days to about 6 days;
(b) a first rest period that includes abstaining from administering the compound for a time period of from about 1 day to about 3 days;
(c) a second treatment cycle that includes administering the effective amount of the compound for a time period of from about 4 days to about 6 days; and
(d) a second rest period that includes abstaining from administering the compound for a time period of at least about 8 days, thereby treating the blood cancer in the subject.

2. The method of claim 1, wherein the effective amount is of from about 5 mg/m² to no more than about 30 mg/m² per 24 hour time period.

3. The method of claim 1, wherein the effective amount is administered in a single dose.

4. The method of claim 1, wherein the effective amount is administered via a plurality of doses.

5. The method of claim 1, wherein the effective amount is administered via a single dose on some days and via a plurality of doses on other days.

6. The method of claim 1, wherein the leukemia is acute lymphocytic leukemia, acute myelogenous leukemia, chronic lymphocytic leukemia, or chronic myeloid leukemia.

7. The method of claim 1, wherein the therapeutically effective amount is of from about 1.25 mg/m² to about 5 mg/m².

8. The method of claim 1, wherein the blood cancer is myelodysplastic syndrome.

9. The method of claim 1, wherein the blood cancer is multiple myeloma or solitary myeloma.

10. A method of treating a blood cancer in a human subject in need thereof, the method comprising administering to the subject an effective amount of a compound having a structure:

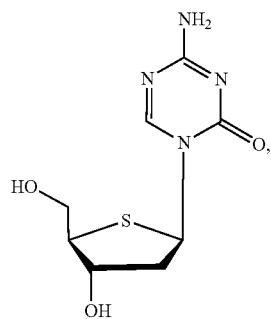

wherein the effective amount is of from about 1.25 mg/m² to less than 5 mg/m² per 24 hour time period, thereby treating the blood cancer in the subject.

* * * * *